United States Patent [19]

Schlechtriemen et al.

[11] Patent Number: 4,792,752
[45] Date of Patent: Dec. 20, 1988

[54] SENSOR FOR MEASURING PARTIAL PRESSURES OF GASES

[75] Inventors: Gerhard-Ludwig Schlechtriemen, Lübeck; Werner Weppner, Stuttgart; Helmut Schubert, Leonberg, all of Fed. Rep. of Germany

[73] Assignees: Drager AG; Max-Planck-Gesellschaft zur Forderüng der Wissenschaften e.v., both of Fed. Rep. of Germany

[21] Appl. No.: 940,483

[22] Filed: Dec. 9, 1986

[30] Foreign Application Priority Data

Dec. 12, 1985 [DE] Fed. Rep. of Germany ....... 3543818

[51] Int. Cl.⁴ ............................................. G01N 27/00
[52] U.S. Cl. ..................................... 324/71.1; 264/43; 264/60; 264/82; 264/272.17
[58] Field of Search .................. 324/71.1; 264/43, 60, 264/82, 272.17

[56] References Cited

U.S. PATENT DOCUMENTS 4,370,393 1/1983 Watanabe et al. ............... 501/103 X
4,668,374 5/1987 Bhagat et al. ..................... 357/25 X Primary Examiner—A. D. Pellinen
Assistant Examiner—Morris Ginsburg
Attorney, Agent, or Firm—McGlew and Tuttle

[57] ABSTRACT

A sensor for measuring partial pressures of oxygen with an ion-conducting solid electrolyte of zirconium dioxide as the sensor element, which is arranged between two electrodes for measuring an electrically measurable quantity, is improved so that it is usable at an operating temperature of about 200° C., by providing that the zirconium dioxide as the solid electrolyte is solely in its tetragonal modification and containing an addition of about 2-3 mol % yttrium oxide.

7 Claims, 2 Drawing Sheets

SENSOR FOR MEASURING PARTIAL PRESSURES OF GASES

FIELD AND BACKGROUND OF THE INVENTION

This invention relates in general to gas sensors and in particular to a new and useful gas sensor having a solid electrolyte of tetragonal zirconium dioxide.

The invention particularly concerns a sensor for measuring partial pressures of gases, especially partial pressures of oxygen, with an ion-conducting solid electrolyte of zirconium dioxide as the sensor element, which is arranged between two electrodes for measuring an electrically measurable quantity.

A similar sensor arrangement of this kind has been known from German OS No. 28 37 593. In the previously known gas sensors using zirconium dioxide as the solid electrolyte, use is principally made of the conductivity of the cubic modification of zirconium dioxide. Additions of calcium, magnesium or yttrium oxide in high concentrations of about 8–9 mol % are used to stabilize the cubic zirconium dioxide. Such a stabilized cubic modification of zirconium dioxide is used for reasons of thermoshock stability and mechanical stability of the gas sensor. Because of the lower valency of the dopant metal ions, vacancies are generated in the oxygen sublattice of the solid electrolyte, across which a transfer of gas ions, especially oxygen ions, is possible by means of a vacancy mechanism. The known gas sensors are used to measure the oxygen in the exhaust gases from internal-combustion engines or in flue-gas from furnaces. The optimal operating temperature for the known gas sensors lies between 800° and 1000°. In operation, these sensors have to withstand high temperature changes, so that a high demand is put on the thermoshock stability of the solid electrolyte of zirconium dioxide used.

Since the specific resistivity of stabilized cubic zirconium dioxide increases rapidly with decreasing temperature, because of the high activation energy of the conductivity, it was attempted to lower the cell impedance by reducing the electrolyte thickness, using methods from thin- or thick-film technology. However, the operating temperature of the sensors could not thereby be satisfactorily decreased. The reason for this clearly lies in that the rate determining step of the incorporation of gas molecules at the electrodes from the gas phase in the solid electrolyte cannot be modified by this approach. The transfer of the gas into the lattice structure of the solid electrolyte is severely inhibited at temperature significantly below 500° C.

It is known to add a small proportion of tetragonal zirconium dioxide to the stabilized cubic zirconium dioxide for reasons of the increase in mechanical stability, thereby creating a heterogenious two-phase system. However, the ion conductivity is in this case likewise achieved exclusively through the stabilized cubic modification of zirconium dioxide.

SUMMARY OF THE INVENTION

The invention provides an improved gas sensor with a solid electrolyte of zirconium dioxide usable at an operating temperature of about 200° C. to 300° C.

The zirconium dioxide as the solid electrolyte is solely in its tetragonal modification i.e. there is a homogeneous single phase, which is formed by an addition of about 2–3 mol % yttrium oxide ($Y_2O_3$).

Contrary to the general expectation of person skilled in this art, it has been found that the conductivity of such a tetragonal phase of zirconium dioxide is of the same order of magnitude as the conductivity of the known highly doped cubic modification of zirconium dioxide. Since, of course, the tetragonal modification of zirconium dioxide is present with substantially lower concentrations of the stabilizing additives, e.g. between 2 and 3 mol % of yttrium oxide, the concentration of the oxygen ion vacancies in the oxygen sublattice is also low, so that a lower conductivity for oxygen ions was expected, compared with that found in the known more highly doped, between 7 and 8 mol % yttrium oxide as additive, cubic modification of zirconium dioxide.

A solid electrolyte sensor working potentiometrically, whose solid ionic conductor comprises tetragonal zirconium dioxide, already shows an attainment of the equilibrium-emf within seconds or minutes at comparatively low operation temperatures between 200° and 300° C. Clearly, with tetragonal zirconium dioxide the substantially more favorable conditions are present for sufficiently rapid kinetics of the incorporating steps between the gas phase and the solid electrolyte, necessary for the attainment of a stable voltage.

The arrangement of an oxygen sensor with tetragonal zirconium dioxide as the oxygen-ion conductor is described in accordance with the formation of a concentration cell as follows:

| reference electrode | tetragonal $ZrO_2$ | Pt (porous) |
|---|---|---|
| Pt | | $PO_2$ (test gas) |

For the generation of a reference partial pressure of oxygen, air can be used, for example, which by means of porous platinum interacts with the tetragonal $ZrO_2$. For this purpose, a tetragonal $ZrO_2$ disc was fused into a Duran glass tube by using transition glasses. Alternatively, mixtures of metals with their metal oxides which likewise produce a definite partial pressure of oxygen can also be used as reference. A porous platinum layer is placed on the measuring side in a way similar to that using the cubic $ZrO_2$. At the 3-phase boundary, where the solid electrolyte, platinum and the gas phase are all in contact, electrons can be exchanged and an incorporation of oxygen from the gas phase into the electrolyte is obtained. By means of the different structure of the zirconium dioxide used here, the kinetics of this process is substantially faster in this case than with the use of the cubic $ZrO_2$.

Under isothermal conditions, the electric potential difference, designated emf in the limiting case of the currentless measurement, between the two leads is related to the partial pressure of oxygen in the test gas ($PO_2$) and the partial pressure of oxygen at the reference electrode ($PO'_2$) according to the Nernst equation as follows:

$$E = \frac{RT}{4F} \ln \frac{PO_2}{PO'_2}$$

According to the invention the tetragonal $ZrO_2$ ceramic is produced from the co-precipitated powders of 97 mol % and $ZrO_2$ and 3 mol % $Y_2O_3$ (Toyo Soda Manufacturing Company TZ-3Y). Applying a pressure of 630 MPa the (cold-isostatically pressed), greens or ceramic materials, in pretreatment form were sintered in air at a temperature of 1400° C. for two hours. In addition, samples were pre-sintered at 1400° C. for 15 minutes in air and subsequently hot-isostatically pressed in an argon gas atmosphere at 1200°–1500° C. for a period of 1 minute to 2 hours. After that a reoxidation under atmosphere gas is performed.

Accordingly, it is an object of the invention to provide a sensor for measuring partial pressures of gases and especially partial pressures of oxygen which comprises a sensor element of an ion-conducting solid electrolyte of zirconium dioxide where two electrodes are in contact with the opposite surfaces of the solid ionic conductor and wherein the zirconium dioxide electrolyte is in its tetragonal modification and has an addition of about 2–3 mol % of yttrium oxide ($Y_2O_3$).

A further object of the invention is to provide a sensor for measuring gas partial pressure which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
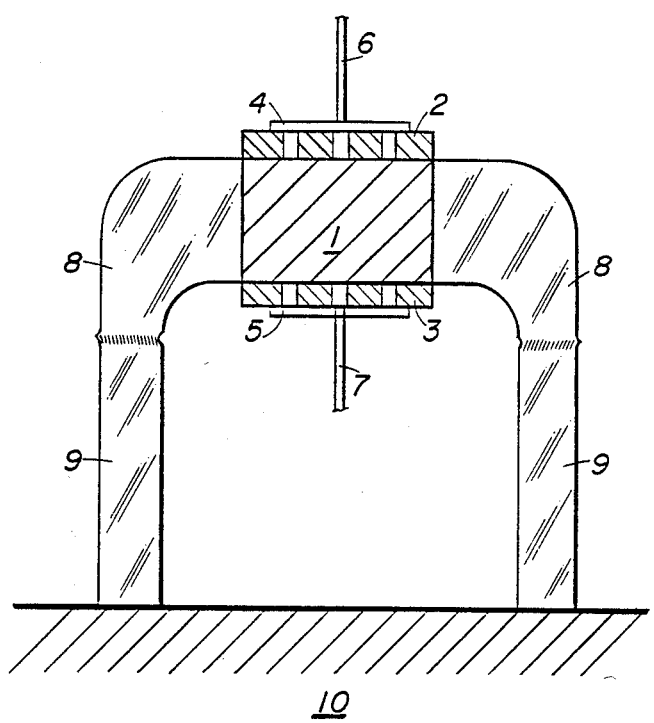
FIG. 1 is a schematic sectional view of the arrangement of a gas sensor in accordance with the invention.

Referring to the drawings in particular the invention as embodied therein comprises a sensor for measuring partial pressures of gases especially partial pressures of oxygen and which includes a solid electrolyte of zirconium dioxide 1 which is solely in its tetragonal modification and has an addition of about 2–3 mol % yttrium oxide.

The tetragonal $ZrO_2$ ceramic was produced from the coprecipitated powders of 97 mol % and $ZrO_2$ and 3 mol % $Y_2O_3$ (Toyo Soda Manufacturing Company TZ-3Y). Applying a pressure of 630 MPa the (cold-isostatically pressed), greens or ceramic materials, in pretreatment form were sintered in air at a temperature of 1400° C. for two hours. In addition, samples were pre-sintered at 1400° C. for 15 minutes in air and subsequently hot-isotatically pressed in an argon gas atmosphere at 1200°–1500° C. for a period of 1 minute to 2 hours. After that a reoxidation under atmosphere gas is performed.

In FIG. 1 a gas sensor is represented which has a solid electrolyte 1 of tetragonal zirconium dioxide a ceramic of 97 mol % $ZrO_2$ and 3 mol % $Y_2O_3$, on the two frontal surfaces of which are placed measuring electrodes 2 and 3 of porous platinum. The test gas, for example, has access to the solid electrolyte through the one measuring electrode 2, while the second electrode 3 is exposed to, for example, air as reference gas. Lead electrodes 4 and 5 are in contact with the two electrodes 2 and 3, a signal from the lead electrodes being transmitted over connecting wires 6 and 7 to an evaluating unit (not shown). The gas sensor is connected with a support 10 by glass junctions 8 and 9. It has been seen that the material of the solid electrolyte, i.e. tetrogonal zirconium dioxide, in contrast to the known stabilized cubic zirconium dioxide, is especially suitable for generation of forming a direct connection with glass. To that end a first glass junction of transition glass is first fused onto the solid electrolyte, followed by a second glass junction 9 for a further connection to the support 10.

Figure 2:
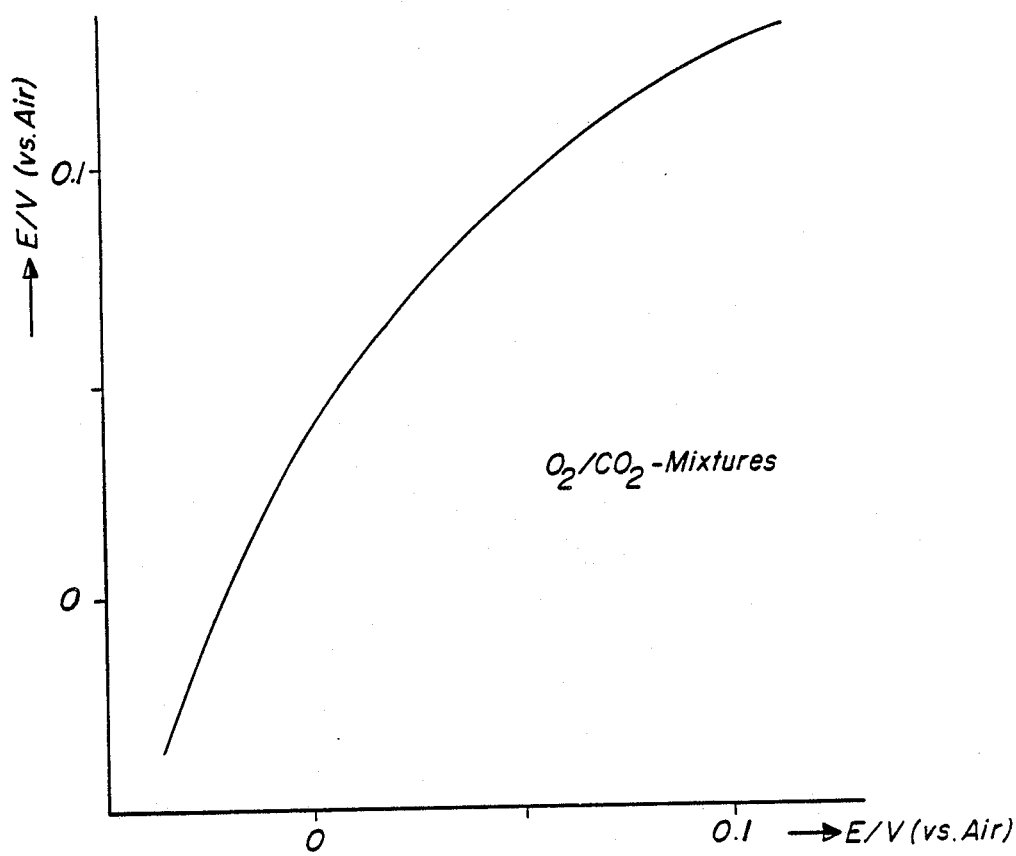
FIG. 2 is a comparative diagram for a determination of the oxygen partial pressure.

A comparative measurement between a known gas sensor with stabilized cubic zirconium dioxide and a gas sensor with tetragonal zirconium dioxide is shown in FIG. 2. The emf measuring values (in volts) obtained for different oxygen partial pressures in the test gas using a cell with stabilixzed cubic $ZrO_2$ (reference gas air) are plotted on the abscissa, as they were obtained at an operating temperature of 800° C.

On the ordinate are plotted the corresponding measuring results which were obtained with a gas sensor that was exposed to partial pressures of oxygen existing in the reaction gas mixtures of $O_2/CO_2$, containing, however, a solid electrolyte of tetragonal zirconium dioxide, and held at an operating temperature of only 300° C. The equilibrium attainment of the sensor with tetragonal zirconium dioxide during the measurement is very rapid, especially in the region of low partial pressures of oxgyen, and proceeds within the required time for the variation in the partial pressure of oxygen caused by changing the composition of the test gas, i.e. within seconds, even at operating temperatures of 200° C. At higher partial pressures of oxygen in the concentration range of the surrounding air the equilibrium attainment is of the order of magnitude of a few minutes.

While specific embodiments of the invention have been shown and described in detail to illustrate the application of the principles of the invention, it wil be understood that the invention may be embodied otherwise without departing from such principles.

What is claimed is:

1. A sensor for measuring partial pressures of oxygen in a mixture of gases, comprising: a sensor element of an ion-conducting solid electrolyte of single phase tetragonal zirconium dioxide which is formed by an addition of about 2–3 mol % of yttrium oxide ($Y_2O_3$) to zirconium dioxide; a first electrode engaged with said sensor element; a second electrode engaged with said sensor element spaced from said first electrode whereby said first and second electrode are used for measuring an electrically measurable quantity.

2. A sensor according to claim 1, wherein: said first and second electrodes are each formed of porous platinum.

3. A sensor according to claim 1, further comprising a glass support connected to said sensor element to form a glass-ceramic junction.

4. A process for the production of a sensor for measuring partial pressures of oxygen in a mixture of gases, comprising the steps of: forming an ion conducting solid electrolyte as a sensor element of tetragonal zirconium dioxide by forming a mixture of 97 mol % zirconium dioxide with 3 mol % yttrium oxide, pressing the mixture cold-isostatically under a pressure of 630 MPa to a pretreatment form material, sintering the material in the pretreatment form in air at a temperature of 1400° C. for two hours; positioning a first electrode element in engagement with a first side of said sensor element and positioning a second electrode in engagement with a second side of said sensor element for measuring an electrically measurable quantity.

5. A process for the production of a sensor according to claim 4, further comprising: pressing the mixture of 97 mol % zirconium dioxide with 3 mol % yttrium oxide cold-isostatically under a pressure 630 MPa to a green form which is pre-sintered in air at a temperature 1400° C. for fifteen minutes; and, subsequently pressing the pre-sintered compound hot-isostatically in an argon gas atmosphere in a temperature range between 1200° and 1500° C. for a time period between one minute and two hours, and thereafter carrying out a re-oxidation in the presence of atmospheric gas.

6. A method according to claim 4, wherein, said ion conducting solid electrolyte formed solely consists of pure tetragonal zirconium dioxide and is formed as a single phase, homogeneous, system.

7. A sensor for measuring partial pressures of oxygen in a mixture of gases, comprising: a sensor element of an ion-conducting solid electrolyte of single phase homogeneous tetragonal zirconium dioxide which is formed by an addition of about 2-3 mol % of yttrium oxide ($Y_2O_3$) to zirconium dioxide; a first electrode engaged with said sensor element; a second electrode engaged with said sensor element spaced from said first electrode whereby said first and second electrode are used for measuring an electrically measurable quantity.

* * * * *